US005534427A

United States Patent [19]
Johnston et al.

[11] Patent Number: 5,534,427
[45] Date of Patent: Jul. 9, 1996

[54] PSEUDOMONAS FLUORESCENS LIPASE

[75] Inventors: Robert M. Johnston, Whitehouse Station; Steven L. Goldberg, Gillette; Paul M. Cino, Bound Brook, all of N.J.

[73] Assignee: E. R. Squibb & Sons, Inc., Princeton, N.J.

[21] Appl. No.: 923,120

[22] Filed: Jul. 31, 1992

[51] Int. Cl.⁶ .............................. C12N 9/20; C12N 15/55; C12N 15/70
[52] U.S. Cl. .................. 435/198; 435/320.1; 536/23.2
[58] Field of Search ..................................... 435/198, 197, 435/320.1; 536/23.2

[56] References Cited

FOREIGN PATENT DOCUMENTS

| | | |
|---|---|---|
| 0407225A1 | 1/1991 | European Pat. Off. . |
| 0443063A1 | 8/1991 | European Pat. Off. . |
| 0451452A1 | 10/1991 | European Pat. Off. . |
| WO91/00908 | 1/1991 | WIPO . |

OTHER PUBLICATIONS

G. H. Chung et al., Agric. Biol. Chem., vol. 55, No. 9, pp. 2359–2365, 1991.
Y. Tan et al., Applied and Environmental Microbiology, vol. 58, No. 4, pp. 1402–1407, Apr. 1992.
G. H. Chung et al., Applied Microbiology and Biotechnology, vol. 35, pp. 237–241, 1991.
L. A. Johnson et al., Applied and Environmental Microbiology, vol. 58, No. 5, pp. 1776–1779, May 1992.
L. G. J. Frenken et al., Applied and Environmental Microbiology, vol. 58, No. 12, pp. 3787–3791, Dec. 1992.
M. Sugiura et al., Biochimics et Biophysics Acta., vol. 488, pp. 353–358, 1977.
M. Sugiura et al., Biochimics et Biophysics Acta, vol. 489, pp. 262–268, 1977.
F. Bozoglu et al., J. Agric. Food Chem., vol. 32, No. 1, pp. 2–6, 1984.
T. Suzuki et al., Applied Microbiology and Biotechnology, vol. 27, pp. 417–422, 1988.
CAS BioTech Updates—Genetic Engineering, No. 5216, Issue 16, p. 2, 1991.
CAS BioTech Updates—Genetic Engineering, No. 5242, Issue 16, p. 5, 1991.
S. Jorgensen et al., Journal of Bacteriology, Vo.. 173, No. 2, pp. 559–567, Jan. 1991.
S. Aoyama et al., FEBS Letters, vol. 242, No. 1, pp. 36–40, Dec. 1988.
W. Kugimiya et al., Biochemical and Biophysical Research Communications, vol. 141, No. 1, pp. 185–190, Nov. 26, 1986.
T. Iizumi et al., Agric. Biol. Chem., vol. 55, No. 9, pp. 2349–2357, 1991.
T. Iizumi et al., Agric. Biol. Chem., vol. 54, No. 5, pp. 1253–1258, 1990.
T. Nishio et al., Agric. Biol. Chem., vol. 51, No. 1, pp. 181–186, 1987.
M. Kordel et al., Journal of Bacteriology, vol. 173, No. 15, pp. 4836–4841, Aug. 1991.
T. Nishio et al., Agric. Biol. Chem., vol. 52, No. 5, pp. 1203–1208, 1988.
Difeo Manual (1984), 10th edition, pp. 874–875.
Lee, C. C., et al. (1988) Science 239, 1288–1291.
Suggs, S. V., et al. (1981) Proc. Natl. Acad. Sci. USA 78(11), 6613–6617.

*Primary Examiner*—Charles L. Patterson, Jr.
*Attorney, Agent, or Firm*—Timothy J. Gaul

[57] ABSTRACT

Nucleic acid sequences, particularly DNA sequences, coding for all or part of a lipase of *Pseudomonas fluorescens*, wherein said lipase has the amino acid sequence encoded by the nucleotide sequence of the BamHI/HindIII insert of the plasmid pRJ-Ltac1 from *Escherichia coli* BL21/pRJ-Ltac1 deposited with the American Type Culture Collection, expression vectors containing the DNA sequences, host cells containing the expression vectors, and methods utilizing these materials. The invention also concerns polypeptide molecules comprising all or part of a lipase of *Pseudomonas fluorescens*, wherein said lipase has the amino acid sequence encoded by the nucleotide sequence of the plasmid pRJ-Ltac1 from *Escherichia coli* BL21/pRJ-Ltac1 BamHI/HindIII insert of deposited with the American Type Culture Collection, and methods for producing these polypeptides.

6 Claims, 4 Drawing Sheets

PSEUDOMONAS FLUORESCENS LIPASE

BACKGROUND OF THE INVENTION

Lipases are a large group of enzymes which are found in many different species. In nature, these enzymes are primarily responsible for catalyzing the conversion of triglycerides to fatty acids. Lipases have been isolated from many different species. For example International Patent Application, Publication No. WO 91/00908, European Patent Application, Publication No. 0 407 225 A1, European Patent Application, Publication No. 0 443 063 A1 and U.S. Pat. No. 5,063,160 all describe the isolation of lipase from various Pseudomonas species. However, there is still a need for lipases which may have more favorable characteristics that those already isolated.

SUMMARY OF THE INVENTION

The present invention concerns an isolated nucleic acid molecule comprising a nucleic acid sequence coding for all or part of a lipase of *Pseudomonas fluorescens*, wherein said lipase has the amino acid sequence (SEQ. ID. NO:2) encoded by the nucleotide sequence (SEQ. ID. NO:1) of the BamHI/HindIII insert of the plasmid pRJ-Ltac1 from *Escherichia coli* BL21/pRJ-Ltac1, deposited with the American Type Culture Collection. (Hereinafter, this insert is referred to as the "Subject Insert"). Preferably, the nucleic acid molecule is a DNA (deoxyribonucleic acid) molecule, and the nucleic acid sequence is a DNA sequence. Further preferred is a DNA sequence having all or part of the nucleotide sequence of the Subject Insert.

The present invention further concerns expression vectors comprising a DNA sequence coding for all or part of a lipase of *P. fluorescens*, wherein said lipase has the amino acid sequence encoded by the nucleotide sequence of the Subject Insert.

The present invention also concerns prokaryotic or eukaryotic host cells containing an expression vector which comprises a DNA sequence coding for all or part of a lipase of *P. fluorescens*, wherein said lipase has the amino acid sequence encoded by the nucleotide sequence of the Subject Insert.

The present invention additionally concerns polypeptide molecules comprising all or part of a lipase of *P. fluorescens*, wherein said lipase has the amino acid sequence encoded by the nucleotide sequence of the Subject Insert.

BRIEF DESCRIPTION OF THE DRAWINGS

FIG. 2 is a restriction map of lipase expression plasmid pRJ-L2. Plasmid pRJ-L2 contains the KpnI/PvuI insert fragment of lipolytic recombinant lambda phage P.f.lip.1. This insert has been placed downstream of the Lac promoter of *E. coli*. The *P. fluorescens* genomic DNA clone is bounded by the EcoRI restriction sites at positions 4.55 and 1.60. Key: "Lac prom."=the lactose promoter sequence; "lambda"=flanking lambda phage DNA; "f1(+)"=the f1(+) origin, "chloram."=chloramphenicol resistance gene; "ColE1"=the origin of replication from plasmid ColE1; "Kb"=kilobase (1000 base pairs).

FIG. 6 is a restriction map of lipase expression plasmid pRJ-Ltac1. Plasmid pRJ-Ltac1 contains the XhoI/PvuII insert fragment of plasmid pRJ-L21. The lipase gene has been placed under the control of the tac promoter sequence. *E. coli* transformed with plasmid pRJ-Ltac1 are highly lipolytic. Key: "ptac"=the tac promoter sequence; "Lipase"= the *P. fluorescens* lipase insert fragment; "lambda=flanking lambda phage DNA; "5S/rrn"=transcriptional termination sequence; "Amp."=ampicillin resistance gene; "pBR322 ori"=the origin of replication from plasmid pBR322. Restriction sites shown in parentheses are no longer functional.

DETAILED DESCRIPTION OF THE INVENTION

The present invention concerns an isolated nucleic acid molecule comprising a nucleic acid sequence coding for all or part of a lipase of *P. fluorescens*, wherein said lipase has the amino acid sequence encoded by the nucleotide sequence of the Subject Insert. Preferably, the nucleic acid molecule is a DNA molecule and the nucleic acid sequence is a DNA sequence. Further preferred is a DNA sequence having all or part of the nucleotide sequence of the Subject Insert, or a DNA sequence complementary to this DNA sequence. In the case of a nucleotide sequence (e.g., a DNA sequence) coding for part of a lipase of *P. fluorescens*, wherein said lipase has the amino acid sequence encoded by the nucleotide sequence of the Subject Insert, it is preferred that the nucleotide sequence be at least about 15 sequential nucleotides in length, more preferably at least about 20 sequential nucleotides in length or 30 sequential nucleotides in length.

The DNA sequences of the present invention can be isolated from a variety of sources, although the presently preferred sequence has been isolated from genomic DNA obtained from *P. fluorescens* ATCC 13525.

The DNA sequences of the present invention can be obtained using variety methods well-known to those of ordinary skill in the art. At least three alternative principal methods may be employed:

(1) the isolation of a double-stranded DNA sequence from genomic DNA or complementary DNA (cDNA) that contains the sequence;
(2) the chemical synthesis of the DNA sequence; and
(3) the synthesis of the DNA sequence by polymerase chain reaction (PCR).

In the first approach, a genomic DNA library can be screened in order to identify a DNA sequence coding for all or part of a lipase of *P. fluorescens*, wherein said lipase has the amino acid sequence encoded by the nucleotide sequence of the Subject Insert.

Various techniques can be used to screen the genomic DNA library. For example, labeled single stranded DNA probe sequences complementary to or duplicating a sequence present in the target genomic DNA coding for all or part of a lipase of *P. fluorescens*, wherein said lipase has the amino acid sequence encoded by the nucleotide sequence of the Subject Insert, can be employed in DNA/DNA hybridization procedures carried out on cloned copies of the genomic DNA which have been denatured to single stranded form.

A genomic DNA library can also be screened for a genomic DNA coding for all or part of a lipase of *P. fluorescens*, wherein said lipase has the amino acid sequence encoded by the nucleotide sequence of the Subject Insert, using any of several screening techniques.

In one typical screening method suitable for the hybridization techniques, the genomic DNA library, which is usually contained in a vector such as EMBL 3 or EMBL 4, is first spread out on agarose plates, and then the clones are transferred to filter membranes, for example, nitrocellulose membranes. A DNA probe can then be hybridized to the clones to identify those clones containing the genomic DNA coding for all or part of a lipase of *P. fluorescens*, wherein said lipase has the amino acid sequence encoded by the nucleotide sequence of the BamHI/HindIII insert of the Subject Insert.

In the second approach, the DNA sequences of the present invention coding for all or part of a lipase of *P. fluorescens*, wherein said lipase has the amino acid sequence encoded by the nucleotide sequence of the Subject Insert, can be chemically synthesized. For example, the DNA sequence coding for a lipase of *P. fluorescens*, wherein said lipase has the amino acid sequence encoded by the nucleotide sequence of the Subject Insert, can be synthesized as a series of 50–100 base oligonucleotides that can then be sequentially ligated (via appropriate terminal restriction sites) to form the correct linear sequence of nucleotides.

In the third approach, the DNA sequences of the present invention coding for all or part of a lipase of *P. fluorescens*, wherein said lipase has the amino acid sequence encoded by the nucleotide sequence of the Subject Insert, can be synthesized using PCR. Briefly, pairs of synthetic DNA oligonucleotides generally at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. [See, White, T. J. et al., *Trends Genet.* 5, 185–189 (1989)].

The DNA sequences of the present invention can be used in a variety of ways in accordance with the present invention. For example, they can be used as DNA probes to screen other genomic DNA libraries so as to select by hybridization other DNA sequences that code for related proteins.

The DNA sequences of the present invention coding for all or part of a lipase of *P. fluorescens*, wherein said lipase has the amino acid sequence encoded by the nucleotide sequence of the Subject Insert, can also be modified (i.e., mutated) to prepare various mutations. Such mutations may be either degenerate, i.e., the mutation does not change the amino acid sequence encoded by the mutated codon, or non-degenerate, i.e., the mutation changes the amino acid sequence encoded by the mutated codon. Both degenerate and non-degenerate mutations may be advantageous in producing or using the polypeptides of the present invention. For example, these mutations may modify the function of the protein (e.g., result in higher or lower activity), permit higher levels of production, easier purification, or provide additional restriction endonuclease recognition sites. All such modified DNA and polypeptide molecules are included within the scope of the present invention.

These modified DNA sequences may be prepared, for example, by mutating the DNA sequence encoding a lipase of *P. fluorescens*, wherein said lipase has the amino acid sequence encoded by the nucleotide sequence of the Subject Insert, so that the mutation results in the deletion, substitution, insertion, inversion or addition of one or more amino acids in the encoded polypeptide using various methods known in the art. For example, the methods of site-directed mutagenesis described in Taylor, J. W. et al., *Nucl. Acids Res.* 13, 8749–8764 (1985) and Kunkel, J. A., *Proc. Natl. Acad. Sci.* (U.S.A.) 82, 482–492 (1985) may be employed. In addition, kits for site-directed mutagenesis may be purchased from commercial vendors. For example, a kit for performing site-directed mutagenesis may be purchased from Amersham Corp. (Arlington Heights, Ill.). In addition, disruption, deletion and truncation methods as described in Sayers, J. R. et al., *Nucl. Acids Res.* 16, 791–800 (1988) may also be employed.

As used in the present application, the term "modified", when referring to a nucleotide or polypeptide sequence, means a nucleotide or polypeptide sequence which differs from the wild-type sequence found in nature.

The present invention further concerns expression vectors comprising a DNA sequence coding for all or part of a lipase of *P. fluorescens*, wherein said lipase has the amino acid sequence encoded by the nucleotide sequence of the the Subject Insert. The expression vectors preferably contain all or part of the DNA sequence having the nucleotide sequence of the Subject Insert. The expression vectors in general contain one or more regulatory DNA sequences operatively linked to the DNA sequence coding for all or part of a lipase of *P. fluorescens*, wherein said lipase has the amino acid sequence encoded by the nucleotide sequence of the Subject Insert. As used in this context, the term "operatively linked" means that the regulatory DNA sequences are capable of directing the replication and/or expression of the DNA sequence coding for all or part of a lipase of *P. fluorescens*, wherein said lipase has the amino acid sequence encoded by the nucleotide sequence of the Subject Insert.

Expression vectors of utility in the present invention are often in the form of "plasmids", which refer to circular double stranded DNA loops that, in their vector form, are not bound to the chromosome. However, the invention is intended to include such other forms of expression vectors that serve equivalent functions and become known in the art subsequently hereto.

Expression vectors useful in the present invention typically contain an origin of replication, a promoter located in front of (i.e., upstream of) the DNA sequence and followed by the DNA sequence coding for all or part of a lipase of *P. fluorescens*, wherein said lipase has the amino acid sequence encoded by the nucleotide sequence of the Subject Insert, transcription termination sequences and the remaining vector. The expression vectors may also include other DNA sequences known in the art, such as, stability leader sequences, which provide for stability of the expression product, secretory leader sequences which provide for secretion of the expression product; modulatable sequences, which allow expression of the structural gene to be modulated (e.g., by the presence or absence of nutrients or other inducers in the growth medium); marking sequences, which are capable of providing phenotypic selection in transformed host cells; restriction sites for cleavage by restriction endonucleases; and host-specific sequences, which allow expression in various types of hosts, including but not limited to prokaryotes, yeasts, fungi, plants and higher eukaryotes.

The characteristics of the actual expression vector used must be compatible with the host cell which is to be employed. For example, when cloning in a mammalian cell system, the expression vector should contain promoters isolated from the genomic DNA of mammalian cells, (e.g., mouse metallothionien promoter), or from viruses that grow in these cells (e.g., vaccinia virus 7.5K promoter). An expression vector as contemplated by the present invention is at least capable of directing the replication, and preferably the expression, of the DNA sequences of the present invention. Suitable origins of replication include, for example, ColE1 and pMB1 in *E. coli*; 2 µm origin in yeast. Suitable promoters include, for example, Lac, Tac, and T7 in *E. coli*; Gal 1/10 and metallothionein promoters in yeast; CMV 35S and GUS promoters in plants. Suitable termination sequences include, for example, rrnBT$_1$T$_2$ in *E. coli*; SV40 terminator in eukaryotes; CMV 35S terminator in plants; and CYC1 in yeast. As selectable markers, neomycin, ampicillin, and hygromycin resistance can be employed. All of these materials are known in the art and are commercially available.

Suitable commercially available expression vectors into which the DNA sequences of the present invention may be inserted include pBC-SK (Stratagene Cloning Systems), pKK223-3 (Pharmacia LKB Biotechnology), ptrc99A (Pharmacia), pSE380 (Invitrogen Corp.), and the like.

Suitable expression vectors containing the desired coding and control sequences may be constructed using standard recombinant DNA techniques known in the art, many of which are described in Sambrook, et al., *Molecular Cloning: A Laboratory Manual*, Second Edition, Cold Spring Harbor Laboratory, Cold Spring Habor, N.Y. (1989).

The present invention additionally concerns host cells containing an expression vector which comprises a DNA sequence coding for all or part of a lipase of *P. fluorescens*, wherein said lipase has the amino acid sequence encoded by the nucleotide sequence of the Subject Insert. The host cells preferably contain an expression vector which comprises all or part of the DNA sequence having the nucleotide sequence of the Subject Insert. In general, the host cells contain an expression vector comprising one or more regulatory DNA sequences capable of directing the replication and/or the expression of and operatively linked to a DNA sequence coding for all or part of a lipase of *P. fluorescens*, wherein said lipase has the amino acid sequence encoded by the nucleotide sequence of the Subject Insert. Suitable host cells include both prokaryotic and eukaryotic cells. Suitable prokaryotic host cells include, for example, *E. coli* strains W3110-M25, BL21, JM105, Y1090 and the like. Suitable eukaryotic host cells include, for example, CHO cells, HeLa cells, yeast strain DBY746, yeast strain RH218 and the like.

Expression vectors may be introduced into host cells by various methods known in the art. For example, transfection of host cells with expression vectors can be carried out by the calcium phosphate precipitation method. However, other methods for introducing expression vectors into host cells, for example, electroporation, liposomal fusion, nuclear injection, and viral or phage infection can also be employed.

Once an expression vector has been introduced into an appropriate host cell, the host cell may be cultured under conditions permitting expression of large amounts of the desired polypeptide, in this case a polypeptide molecule comprising all or part of a lipase of *P. fluorescens*, wherein said lipase has the amino acid sequence encoded by the nucleotide sequence of the Subject Insert. Such polypeptides are particularly useful in enzymatic processes for the resolution of enantiomeric mixtures of compounds as described hereinbelow and in U.S. patent application Ser. No. 07/822, 015, filed Jan. 15, 1992, entitled "Enzymatic Processes for Resolution of Enantiomeric Mixtures of Compounds Useful as Intermediates in the Preparation of Taxanes", the specification of which is incorporated herein by reference.

Host cells containing an expression vector which contains a DNA sequence coding for a lipase of *P. fluorescens*, wherein said lipase has the amino acid sequence encoded by the nucleotide sequence of the Subject Insert, may be identified by one or more of the following five general approaches: (a) DNA-DNA hybridization; (b) the presence or absence of marker gene functions; (c) assessing the level of transcription as measured by the production of mRNA transcripts encoding a lipase of *P. fluorescens*, wherein said lipase has the amino acid sequence encoded by the nucleotide sequence of the Subject Insert in the host cell; (d) detection of the gene product immunologically; and (e) enzyme assay.

In the first approach, the presence of a DNA sequence coding for all or part of a lipase of *P. fluorescens*, wherein said lipase has the amino acid sequence encoded by the nucleotide sequence of the Subject Insert, can be detected by DNA-DNA or RNA-DNA hybridization using probes complementary to the DNA sequence.

In the second approach, the recombinant expression vector host system can be identified and selected based upon the presence or absence of certain marker gene functions (e.g., thymidine kinase activity, resistance to antibiotics, etc.). A marker gene can be placed in the same plasmid as the DNA sequence coding for all or part of a lipase of *P. fluorescens*, wherein said lipase has the amino acid sequence encoded by the nucleotide sequence of the Subject Insert, under the regulation of the same or a different promoter used to regulate the sequence encoding a lipase of *P. fluorescens*, wherein said lipase has the amino acid sequence encoded by the nucleotide sequence of the Subject Insert. Expression of the marker gene in response to induction or selection indicates expression of the DNA sequence coding for all or part of a lipase of *P. fluorescens*, wherein said lipase has the amino acid sequence encoded by the nucleotide sequence of the Subject Insert.

In the third approach, the production of mRNA transcripts encoding a lipase of *P. fluorescens*, wherein said lipase has the amino acid sequence encoded by the nucleotide sequence of the Subject Insert, can be assessed by hybridization assays. For example, mRNA can be isolated and analyzed by Northern blotting or nuclease protection assay using a probe complementary to the RNA sequence. Alternatively, the total nucleic acids of the host cell may be extracted and assayed for hybridization to such probes.

In the fourth approach, the expression of all or part of the high molecular weight subunit of a lipase of *P. fluorescens*, wherein said lipase has the amino acid sequence encoded by the nucleotide sequence of the Subject Insert, can be assessed immunologically, for example, by Western blotting.

In the fifth approach, expression of the high molecular weight subunit of a lipase of *P. fluorescens*, wherein said lipase has the amino acid sequence encoded by the nucleotide sequence of the Subject Insert, can be measured by assaying for lipase activity using known methods. For example, the assay described hereinbelow may be employed.

The DNA sequences of expression vectors, plasmids or DNA molecules of the present invention may be determined by various methods known in the art. For example, the dideoxy chain termination method as described in Sanger et al., *Proc. Natl. Acad. Sci.* (U.S.A.) 74, 5463–5467 (1977), or the Maxam-Gilbert method as described in *Proc. Natl. Acad. Sci.* (U.S.A.) 74, 560–564 (1977) may be employed.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The present invention further concerns polypeptide molecules comprising all or part of a lipase of *P. fluorescens*, wherein said lipase has the amino acid sequence encoded by the nucleotide sequence of the Subject Insert. In the case of polypeptide molecules comprising part of a lipase of *P. fluorescens*, wherein said lipase has the amino acid sequence encoded by the nucleotide sequence of the Subject Insert, it is preferred that polypeptide molecules be at least about 5 to 8 sequential amino acids in length, more preferably at least about 15 to 20 sequential amino acids in length. Also preferred are polypeptides at least about 180 sequential amino acids in length, which may approximate the size of a structural domain within the protein.

The polypeptides of the present invention may be obtained by synthetic means, i.e., chemical synthesis of the polypeptide from its component amino acids, by methods known to those of ordinary skill in the art. For example, the solid phase procedure described by Houghton et al., *Proc. Natl. Acad. Sci.* (U.S.A.) 82, 5131–5135 (1985) may be employed. It is preferred that the polypeptides be obtained by production in prokaryotic or eukaryotic host cells expressing a DNA sequence coding for all or part of a lipase of *P. fluorescens*, wherein said lipase has the amino acid sequence encoded by the nucleotide sequence of the Subject Insert, or by in vitro translation of the mRNA encoded by a DNA sequence coding for all or part of a lipase of *P. fluorescens*, wherein said lipase has the amino acid sequence encoded by the nucleotide sequence of the Subject Insert. For example, plasmid pRJ-Ltac1 deposited with the American Type Culture Collection, may be used to transform a suitable host cell. The recombinant host cell may then be cultured to produce a lipase of *P. fluorescens*, wherein said lipase has the amino acid sequence encoded by the nucleotide sequence of the Subject Insert. Techniques for the production of polypeptides by these means are known in the art, and are described herein.

The polypeptides produced in this manner may then be isolated and purified using various protein purification techniques. For example, chromatographic procedures such as ion exchange chromatography, gel filtration chromatography and immunoaffinity chromatography may be employed.

The polypeptides of the present invention may be used in a wide variety of ways. For example, the polypeptides may be used to prepare in a known manner polyclonal or monoclonal antibodies capable of binding the polypeptides. These antibodies may in turn be used for the detection of the polypeptides of the present invention in a sample, for example, a cell sample, using immunoassay techniques, for example, radioimmunoassay or enzyme immunoassay. The antibodies may also be used in affinity chromatography for purifying the polypeptides of the present invention and isolating them from various sources.

Due to the degeneracy of the genetic code, other DNA sequences that encode a lipase of *P. fluorescens*, wherein said lipase has the amino acid sequence encoded by the nucleotide sequence of the Subject Insert, may be used for the production of the polypeptides of the present invention. In addition, it will be understood that allelic variations of these DNA and amino acid sequences naturally exist, or may be intentionally introduced using methods known in the art. These variations may be demonstrated by one or more amino acid differences in the overall sequence, or by deletions, substitutions, insertions, inversions or additional of one or more amino acids in said sequence. Such amino acid substitutions may be made, for example, on the basis of similarity in polarity, charge, solubility, hydrophobicity, hydrophilicity and/or the amphiphathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine; asparagine, glutamine; serine, threonine; phenylalanine, tyrosine. Other contemplated variations include salts and esters of the aforementioned polypeptides, as well as precursors of the aforementioned polypeptides, for example, precursors having N-terminal substituents such as methionine, N-formylmethionine and leader sequences. All such variations are included within the scope of the present invention.

The following examples represent preferred embodiments of the invention. These examples are illustrative rather than limiting.

EXAMPLES

A. Description of *P. fluorescens* genomic DNA library

A DNA library composed of random fragments of *P. fluorescens* (Type 2 capsule strain D39, ATCC 13525) genomic DNA was commercially obtained {Clontech Laboratories, Palo Alto, Calif.}. The library was constructed by extracting total genomic DNA from *P. fluorescens* ATCC 13525, mechanically shearing it into random fragments (size range of fragments=1400–6000 base pairs), enzymatically attaching synthetic EcoRI linkers to the ends of the fragments, and inserting these "EcoRI-adapted" fragments into the EcoRI restriction endonuclease recognition site of lambda phage gt11. These recombinant lambda phage particles were used as a "library" from which DNA encoding the *P. fluorescens* lipase gene was isolated.

B. Isolation of recombinant lambda phage that contain DNA encoding the *P. fluorescens* lipase gene

*Escherichia coli* strain Y1090 was grown in maltose-supplemented Luria broth [1.0% Bacto tryptone (Difco Laboratories, Detroit, Mich.); 0.5% Bacto yeast extract (Difco Laboratories, Detroit, Mich.); 0.5% sodium chloride; 0.2% maltose; pH=7.0] at 37° C., on a gyrotory water bath shaker (150 RPM), until growth had reached stationary phase (as determined by optical density at 600 nm). Nine mililiters of this stationary phase culture was transferred to a 15-mL disposable test tube. The recombinant lambda phage library stock solution was diluted 1/5000 in SM suspension medium (0.58% NaCl; 0.2% MgSO4/7H2O; 5% v/v 1M Tds-HCl, pH=7.5; 0.01% gelatin) by adding 3.0 mL of SM medium to 1.5 µL of the phage stock. This 3.0 mL of diluted phage stock (approximate phage count=7.5×10$^6$) was added to the 9.0 mL of saturated $E.$ $coli$ culture and the sample was incubated at 37° C. for 20 minutes (without shaking) to allow cellular attachment of infective phage particles. Following this incubation period, 400 µL aliquots of infected $E.$ $coli$ were withdrawn and added to 3.0 mL of melted top agar (Luria broth plus 7.0 g of agar per liter; top agar was melted at 121° C. for 10 minutes then cooled to 50° C. before addition of cells). The top agar was then poured onto Spirit Blue agar plates [35 g dehydrated Spirit Blue agar and 30 mL of lipase reagent (both Difco Laboratories, Detroit, Mich.), per liter], and the plates were incubated at 35° C. overnight.

Recombinant lambda phage that contained DNA encoding the $P.$ $fluorescens$ lipase gene were identified by a zone of lipolytic clearing within the Spirit Blue agar, in the areas surrounding the infected $E.$ $coli.$ These lipolytic lambda phage particles were then amplified by sequential rounds of infection and isolation. Lipolytic phage isolates were collected by pressing the tip of a sterile Pasteur pipette [1/32 inch internal diameter (Fisher Scientific)] into the center of the zones of clearing and withdrawing an agar plug containing phage particles. Agar plugs were removed from three distinct zones of clearing and each was placed in a 1.5-mL microfuge tube. One mL of SM suspension medium and 10 µL of chloroform was added to each agar plug, and the samples were vortex-mixed [Vortex Genie (Fisher Scientific); speed setting 9] for 2 minutes. These suspensions (presumably enriched for lipolytic phage isolates) were used to infect $E.$ $coli$ strain Y1090 which was plated on a second set of Spirit Blue plates (as described above). Following this second infection, greater than 50% of all infected $E.$ $coli$ showed lipolytic activity, suggesting an enrichment for the specific lipolytic phage particle among the total population of phage particles contained in the agar plug. This infection/agar plug/reinfection procedure was repeated two additional times until 100% of the infected colonies generated from each phage suspension displayed lipolytic activity. At the end of the third amplification, each lipolytic phage suspension was judged to be "pure" (possessing only multiple copies of the same phage isolate).

Serial dilutions of each of the "pure" lipolytic phage stocks were prepared in SM suspension medium. $E.$ $coli$ strain Y1090 was grown to stationary phase in Luria both (37° C., 150 RPM, overnight) and 200 µL aliquots were added to 3.0 mL of top agar. These cell/top agar samples were poured onto LB plates (Luria broth plus 20 gms agar per liter) and allowed to dry for 3 hours at room temperature. When the plates had dried, 10 µL aliquots of the lipolytic phage particle dilutions were spread on the "lawn" of $E.$ $coli.$ These plates were placed at 35° C. overnight. The next day, the plates were examined for signs of cell lysis (phage infection). The number of lysed zones on each plate was used to calculate the total number of infective phage particles present in the 10 µL aliquot of each phage dilution. This number was then used to calculate the "titer" of each lipolytic phage stock.

C. Large scale amplification of recombinant lambda phage containing the $P.$ $fluorescens$ lipase gene The following procedure was performed for each of the three lipolytic lambda phage isolates. A 15 mL culture of $E.$ $coli$ strain Y1090 was grown overnight in maltose-supplemented Luria broth (37° C., 150 RPM) to saturation. A 5.0 mL aliquot of this saturated culture was removed and placed in a 15-mL disposable polypropylene test tube, and 5.0 mL of a 10 mM MgCl$_2$/10 mM CaCl$_2$ solution was added (final concentration of Mg$^{2+}$ and Ca$^{2+}$ ions=5 mM each). A total of 2.0×10$^{10}$ lipolytic phage particles was added and the sample was incubated at 37° C. for 20 minutes with gentle shaking. This entire 10 mL sample was used to inoculate 1000 mL of NZC broth (10 g NZ-amine; 5 gms NaCl; 1 gm casamino acids, per liter; pH=7.0), and the culture was incubated at 37° C. with vigorous shaking (250 RPM) until the culture became dense and then cleared as lambda phage lysed the infected cells. Five mL of chloroform was added to the culture to lyse any remaining intact cells, and the culture was shaken vigorously (250 RPM) at 37° C. for 10 minutes. This culture "lysate" was transferred to 4×250 mL centrifuge bottles and centrifuged at 12,000×g, 4° C., 10 minutes, to pellet cell debris. The supernatant was transferred to a new 1000-ml flask and 29 g of NaCl was added (final concentration=500 mM). This solution was left on a stir plate at 4° C. overnight to allow the NaCl to dissolve. Polyethylene glycol [average molecular weight=3350; (Sigma Chemical Company, St. Louis, Mo.)] was added to a final concentration of 20% by volume, and the flask was placed on ice for 90 minutes to precipitate phage particles. The sample was transferred to 4×250 mL centrifuge bottles and centrifuged at 13,000×g, 4° C., 10 minutes to separate phage particles. The supernate was poured off, and the phage pellet was air-dried at room temperature for 3 hours. The phage pellet was resuspended in 30 mL of lambda diluent (10 mM Tris-HCl; 10 mM MgSO4, pH 7.5) and its titer was determined by spreading aliquots on a lawn of $E.$ $coli$ Y1090 (as described above).

D. Isolation of DNA from lipolytic recombinant phage particles

DNA, representing lambda phage genomic DNA as well as $P.$ $fluorescens$ chromosomal DNA inserts, was extracted from each of the partially purified phage preparations by the following protocol. DEAE-cellulose resin (grade DE-52, Whatman BioSystems Ltd., Kent, England) was prepared by adjusting to 75% resin/25% TM buffer (50 mM Tris-HCl; 10 mM MgSO4, pH 7.5). Nine mililiters of the resin/buffer was dispensed into a 15-mL disposable plastic syringe, allowed to settle, and drained of excess buffer. Six mL of crude phage solution (derived from the large scale preparation) was loaded onto the column and eluted with 10 mL of TM buffer (the first three mL of eluate were "void volume" and were discarded). A total of 13 mL of eluate was collected in a 30-mL glass centrifuge tube, 2 mL of 5M NaCl and 10 mL of ice-cold 100% isopropanol were added and the sample was placed at −20° C. for 15 minutes. The sample was centrifuged at 4000×g, 4° C., for 10 minutes to pellet the purified phage particles. The supernatant was discarded and the phage pellet was air-dried at room temperature for 2 hours.

The purified phage pellet was resuspended in 800 µL of TE buffer (10 mM Tris-HCl, 1 mM ethylenediaminetetraacetic acid, pH 8.0) and extracted once with an equal volume of phenol equilibrated with TE buffer. The aqueous phase was recovered and extracted five times with PCA [50% phenol; 46% chloroform; 4% isoamyl alcohol, equilibrated with TE buffer (Fisher Scientific, Pittsburgh, Pa.)] and twice with 100% chloroform. The aqueous phase was recovered at each step. 3M sodium acetate was added to a total of 1/10 volume, and 2 volumes ice-cold 100% ethanol was added to precipitate the phage DNA. Precipitated phage DNA was collected by twirling onto a clean glass rod, and was subsequently washed once with 70% ethanol. This DNA was air-dried for 2 hours at room temperature and resuspended in a minimal volume of TE buffer. Phage DNA was quantitated by measuring its absorbance at 260 nm (assuming 1.0 OD260 unit is equivalent to 50 µg Of DNA per mL).

E. Isolation of the *P. fluorescens* DNA inserts from purified lipolytic phage DNA Recombinant phage DNA was separated from contaminating RNA by agarose gel electrophoresis. A 0.6% agarose gel was prepared by dissolving 800 mg of agarose (Sigma Chemical Company, St. Louis, Mo.) in 150 mL of TAE/EtBr buffer (40 mM Tris-acetate; 2 mM ethylenediaminetetraacetic acid; 0.5 µg/mL ethidium bromide, pH 8.5) and casting in a horizontal gel electrophoresis platform (Horizon model 11-14, Bethesda Research Laboratories-Life Technologies Inc., Gaithersburg, Md.). Nucleic acid (DNA and RNA) from each lipolytic recombinant phage isolate was loaded into an agarose gel and electrophoresed at 100 Volts for 90 minutes. One kilobase DNA ladder (Bethesda Research Laboratories, Gaithersburg, Md.) run in an adjacent control lane was used to estimate molecular weight. High molecular weight DNA (>10,000 base pairs; representing phage DNA) was visualized by ultraviolet (312 nm) transillumination, and excised from the gel with a razor scalpel. Phage DNA was purified away from the agarose by electroelution [Electrophoresis Gel Eluter, (Fisher Scientific, Pittsburgh, Pa.)] in TAE buffer at 9 mA for 18 hours. Eluted DNA samples were transferred to 1.5 mL microfuge tubes and 1/10 volume of 3M sodium acetate was added. Two volumes of ice-cold ethanol were added and samples were placed at −20° C. for 35 minutes. DNA was pelleted by microcentrifugation at 15,000×g, 15 minutes, room temperature. The supernatant was poured off and the DNA pellet was washed once with 70% ethanol and air-dried for 2 hours at room temperature. The dried phage DNA pellets were resuspended in a minimal volume of TE buffer (50–100 µL).

Recombinant phage DNA was digested with the restriction enzyme EcoRI (Bethesda Research Laboratories, Gaithersburg, Md.) following the manufacturer's recommended reaction conditions. Each of the *P. fluorescens* DNA inserts (contained within the lipolytic recombinant lambda phage particles) is bounded by EcoRI restriction sites. Digestion with EcoRI separated the insert DNA fragments from the lambda phage DNA. The EcoRI-digested DNA was loaded onto a 0.7% agarose gel and electrophoresed in TAE buffer at 10 Volts for 18 hours (as described above). DNA bands were visualized by ultraviolet transillumination and the size of individual *P. fluorescens* insert fragments were estimated by comparison to a 1 kilobase DNA ladder run in a control lane. Two of the recombinant phage contained 2 distinct EcoRI insert fragments, the other recombinant phage appeared to contain only a single insert fragment. The number of insert fragments in each lipolytic recombinant phage as well as the approximate size of those insert fragments is shown below:

| Isolate | Number of Inserts | Approximate Size of Insert (bp-base pairs) |
|---|---|---|
| P.f.lip.1 | 2 | 950 bp, 2000 bp |
| P.f.lip.2 | 1 | 3200 bp |
| P.f.lip.3 | 3 | 1450 bp, 3200 bp |

Each of the insert fragment bands was excised from the gel with a razor scalpel. Insert DNA was purified away from the agarose with Geneclean (BIO 101 Inc., La Jolla, Calif.) according to the manufacturer's protocol and eluted into 50 µL Of TE buffer.

F. Construction of plasmid vectors containing *P. fluorescens* DNA encoding the lipase gene The concentration of DNA in each of the insert fragment suspensions was estimated by running a 1 µL aliquot of the suspension on a 0.6% agarose gel (TAE/EtBr buffer, 80 Volts, 75 minutes), visualizing by ultraviolet (312 nm) transillumination, and comparing its fluorescent emission to that of a fragment of known concentration, which was run in a control lane. Plasmid pBC-SK+ was commercially obtained {Stratagene Cloning Systems, La Jolla, Calif.}; it confers chloramphenicol resistance to transformed *E. coli* and possesses several unique restriction endonuclease recognition sites arranged in a "multiple cloning site". Plasmid pBC-SK+ was digested with EcoRI (Bethesda Research Laboratories, Gaithersburg, Md.), the linearized plasmid DNA was purified with Geneclean (BIO 101 Inc., La Jolla, Calif.), and eluted into TE buffer. DNA concentration was estimated by absorbance at 260 nm.

Each of the *P. fluorescens* insert fragments was ligated into the linearized pBC-SK+ plasmid by the following protocol: 100 ng linearized plasmid DNA was mixed in a 1.5 mL microfuge tube with a 1:1 molar equivalent of insert DNA; 3 µL of 5× T4 DNA ligase reaction buffer [Bethesda Research Laboratories, Gaithersburg, Md.] (final concentration of buffer components at 1× concentration=66 mM Tris-Cl, pH=7.6; 6.6 mM MgCl$_2$; 10 mM dithiothreitol; 66 µM adenosine triose phosphate); 1.5 µL of T4 DNA ligase [(Bethesda Research Laboratories, Gaithersburg, Md.), approximately 1.5 ligase units], and sufficient sterile distilled water to bring the total volume to 15 µL. Ligation reactions were incubated at room temperature for 2.5 hours.

Competent *E. coli* {strain XL-1 Blue; (Stratagene Cloning Systems Inc, La Jolla, Calif.)} were prepared according to the procedure of Chung et. al., *Proc. Natl. Acad. Sci.* (U.S.A.) 86, 2172 (1989). A single colony of XL-1 Blue was innoculated into 2.0 mL of Luria broth supplemented with 12.5 µg/mL tetracycline. This culture was grown at 30° C. overnight on a gyrotory shaker (200–250 RPM). A 1/100 dilution of the overnight culture was made into fresh Luria broth (plus 12.5 µg/mL tetracycline) and this subculture was incubated at 30° C. on a gyrotory shaker (250 RPM) until the OD600 had reached 0.3–0.4. At this point, the cells were centrifuged at 8000×g, 5 minutes, 4° C. The supernatant was discarded and the cell pellet was resuspended in 1/10 volume TSS buffer (Luria broth plus 20% by weight polyethylene glycol (average molecular weight=3350, Sigma Chemical Company, St. Louis Mo.), 100 mM MgHCl$_2$, and 10% by volume dimethyl sulfoxide; pH=6.5). This "competent" cell suspension was kept at 0° C. until used for transformation.

Transformation reactions were prepared by transferring 150 µL of competent XL-1 Blue to a pre-chilled Falcon 2059 polypropylene snap-cap tube and adding the entire 15 µL ligation reaction. Ligation reactions were placed on ice for 30 minutes. Transformant recovery was accomplished by adding 900 μL SOC medium [2.0% Bacto tryptone (Difco Laboratories, Detroit, Mich.), 0.5% Bacto yeast extract (Difco Laboratories, Detroit, Mich.); 20 mM glucose; 10 mM NaCl; 10 mM $MgCl_2$; 10 mM $MgSO_4$; 2.5 mM KCl] and incubating on a water bath shaker (150 RPM) at 30° C. for 90 minutes. Aliquots of 2, 20, 100, and 200 μL were spread onto LB agar plates (plus 100 μg/mL chloramphenicol) to select for chloramphenicol resistant transformants. Only those cells which had incorporated a religated plasmid were able to form colonies. Both recombinant (possessing a *P. fluorescens* DNA insert) and non-recombinant (religated vector alone) transformants were able to grow on chloramphenicol supplemented agar plates.

To determine if transforming plasmids had incorporated *P. fluorescens* DNA insert fragments, small scale cultures of chloramphenicol-resistant *E. coli* transformants were prepared for plasmid "mini-preps". Chloramphenicol-resistant colonies from each of the transformation reactions were used to inoculate 2.0 mL cultures of Luria broth (plus 100 μg/mL chloramphenicol). These cultures were grown on a gyrotory water bath shaker (150 RPM, 37° C., overnight) and plasmid DNA samples were prepared by a modification of the procedure of Birnboim and Doly, *Nucleic Acids Res.* 7, 1513 (1979). Each overnight culture was used to prepare a new LB/chloramphenicol stock plate which was grown at 37° C. overnight and then stored at 4° C.

A 1.0 mL aliquot of each overnight culture was transferred to a 1.5 mL microcentrifuge tube and the cells were pelleted by microcentrifugation at 13,000×g, 5 minutes, room temperature. The supernatant was removed by vacuum aspiration and the cell pellet was resuspended in 100 μL of a solution composed of 50 mM glucose/25 mM Tris-HCl (pH=8.0)/10 mM ethylenediaminetetraacetic acid (pH=8.0). After incubation for 5 minutes at room temperature, 200 μL of a solution composed of 0.2N NaOH/1.0% sodium dodecyl sulfate was added, the tube was shaken gently for 10 seconds then placed on ice for 15 minutes. 150 μL of ice-cold precipitation solution (600 mL 5M potassium acetate; 115 mL glacial acetic acid, per liter, in dH2O) was added and the tubes were placed on ice for 15 minutes. Cellular debris was precipitated by microcentrifugation at 13,000×g, 7.5 minutes, room temperature, and the supernatant was removed to a 1.5-mL new microfuge tube. This supernatant was extracted three times with an equal volume of PCA and once with an equal volume of chloroform, saving the aqueous phase at each step. Plasmid DNA was precipitated from the aqueous phase by the addition of ⅒ volume 5M NaCl and 2 volumes of ice-cold ethanol. Samples were placed at −20° C. overnight. Plasmid DNA was pelleted by microcentrifugation at 13,000×g, 15 minutes, room temperature. The supernate was removed and the plasmid pellet was washed once with 70% ethanol. The pellet was air-dried at room temperature for three hours and resuspended in 50 μL TE buffer plus 20 μg/mL RNase (Bethesda Research Laboratories, Gaithersburg, Md.). Plasmid DNA was digested with restriction endonuclease EcoRI (Bethesda Research Laboratories, Gaithersburg, Md.) and analyzed by agarose gel electrophoresis (as previously described) to determine which plasmid isolates had incorporated the *P. fluorescens* DNA inserts. Only those transformant cultures which generated plasmids which displayed a DNA band in addition to the pBC-SK+ (vector) band were selected for further analysis.

LB/chloramphenicol master plates were retrieved from 4° C. storage and colonies from recombinant transformants were streaked onto Spirit Blue/chloramphenicol plates to determine if they produced lipolytic activity (as described above). After 48 hours at 35° C. none of the recombinant transformants displayed lipolytic activity suggesting that none of the EcoRI insert fragments encompassed he entire lipase gene due to the presence of an EcoRI restriction site within the lipase coding sequence.

Figure 1:
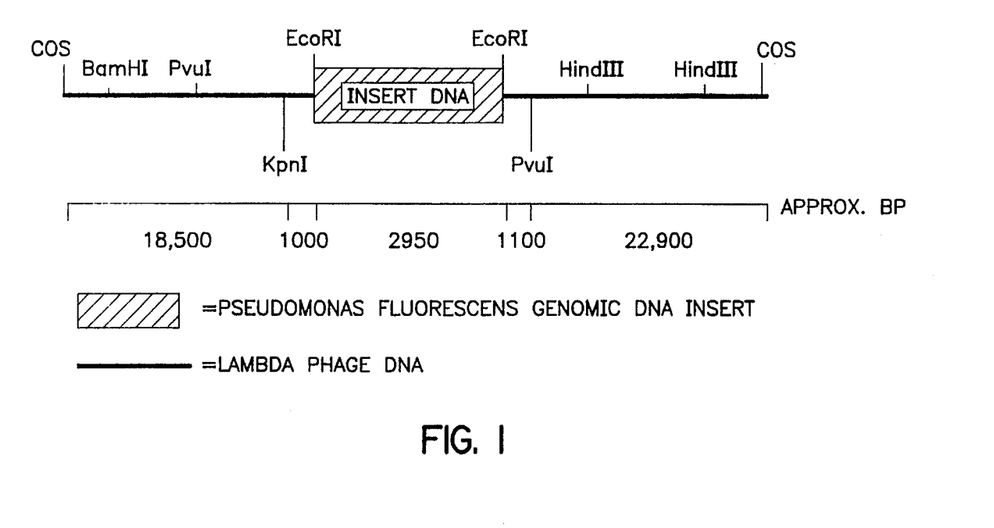
FIG. 1 is a restriction map of DNA extracted from recombinant lipolytic lambda phage P.f.lip.1, showing the relative position of the EcoRI fragment of *P. fluorescens* DNA within the recombinant lambda phage genome. The positions of the flanking KpnI and PvuI sites are indicated. The scale bar under the restriction map shows approximate distances (in base pairs, bp) between the indicated restriction sites. COS=cohesive end.

DNA prepared from lipolytic recombinant phage P.f.lip. 1 was digested with restriction enzymes KpnI (Bethesda Research Laboratories, Gaithersburg, Md.) and PvuI (New England Bio Labs, Beverly, Mass.) according to the manufacturer's recommended reaction conditions. KpnI and PvuI cut lambda gt11 DNA on alternate sides of the EcoRI restriction site (see FIG. 1).

Figure 2:
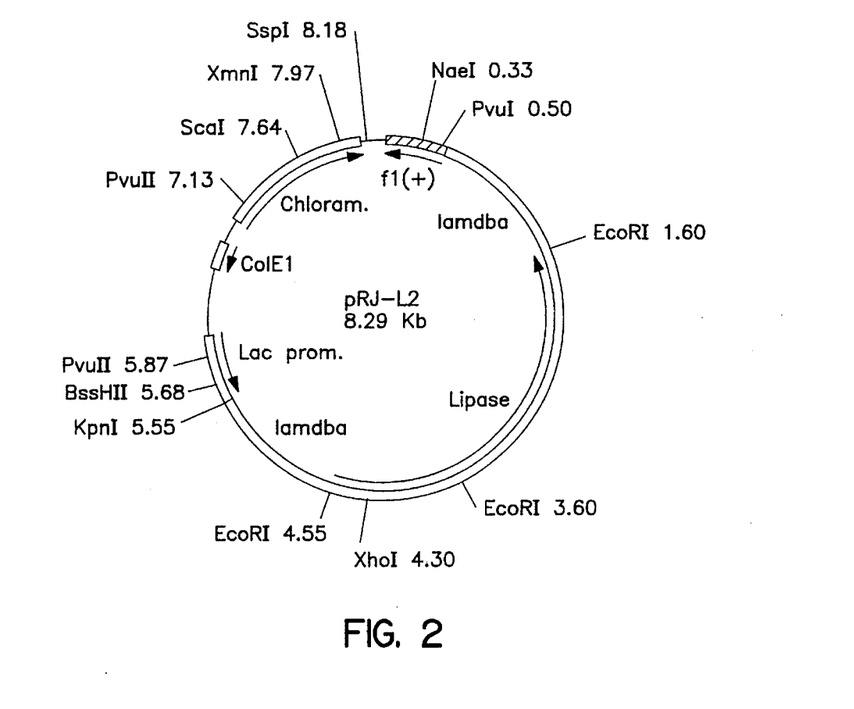

The double digestion of recombinant phage DNA liberated the *P. fluorescens* DNA insert as well as approximately 2100 bp of phage DNA. The KpnI/PvuI insert fragment was separated from lambda genomic DNA by agarose gel electrophoresis (as described above), purified away from the agarose with Geneclean (BIO 101, La Jolla, Calif.), and eluted into TE buffer. This insert fragment (approximate molecular weight=5300 bp) was ligated into a KpnI/PvuI cut pBC-SK+ plasmid (as described above). Religated plasmids were used to transform *E. coli* strain W3110-M25 (made competent by the procedure of Chung et. al., supra). Possible transformants were plated on Spirit Blue/chloramphenicol plates to select both chloramphenicol resistance (implying the presence of a religated plasmid) and lipolytic activity implying the presence of an intact *P. fluorescens* lipase gene insert). Following incubation overnight at 35° C., all transformed colonies were found to be lipolytic. The recombinant plasmid was isolated and purified by a "miniprep" (as described above) and was named pRJ-L2. A diagram of plasmid pRJ-L2 appears in FIG. 2.

G. Restriction analysis of the DNA fragment which encompasses the *P. fluorescens* lipase gene and generation of subclones capable of producing lipase in transformed *E. coli*

Figure 3:
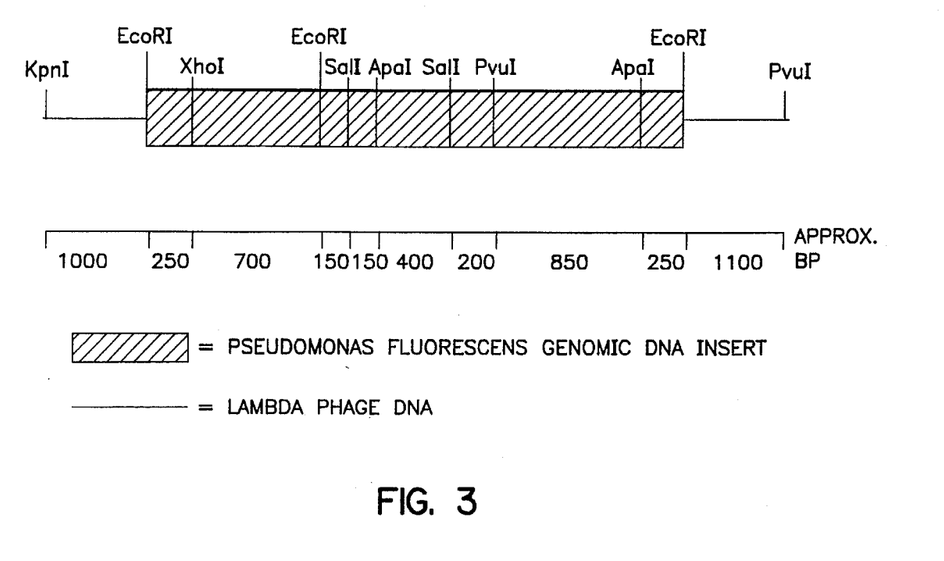
FIG. 3 is a restriction map of the KpnI/PvuI insert fragment of lipase expression plasmid pRJ-L2, showing the relative position of the internal restriction sites of pRJ-L2. The scale bar under the restriction map shows the approximate distance (in base pairs) between each of the restriction sites.

Plasmid pRJ-L2 was digested with a variety of restriction endonucleases (obtained from Bethesda Research Laboratories, Gaithersburg, Md.; New England Bio Labs, Waverly, Mass.; and Promega Corporation, Madison, Wis.; all used according to manufacturer's recommended conditions). The products of the digestion reactions were separated by agarose gel electrophoresis (as previously described). The molecular weights of the restriction fragments were estimated by comparison to a one kilobase ladder size standard (Bethesda Research Laboratories, Gaithersburg, Md.) which was run in a control lane. The results of these analyses were used to generate the restriction map shown in FIG. 3.

Figure 4:
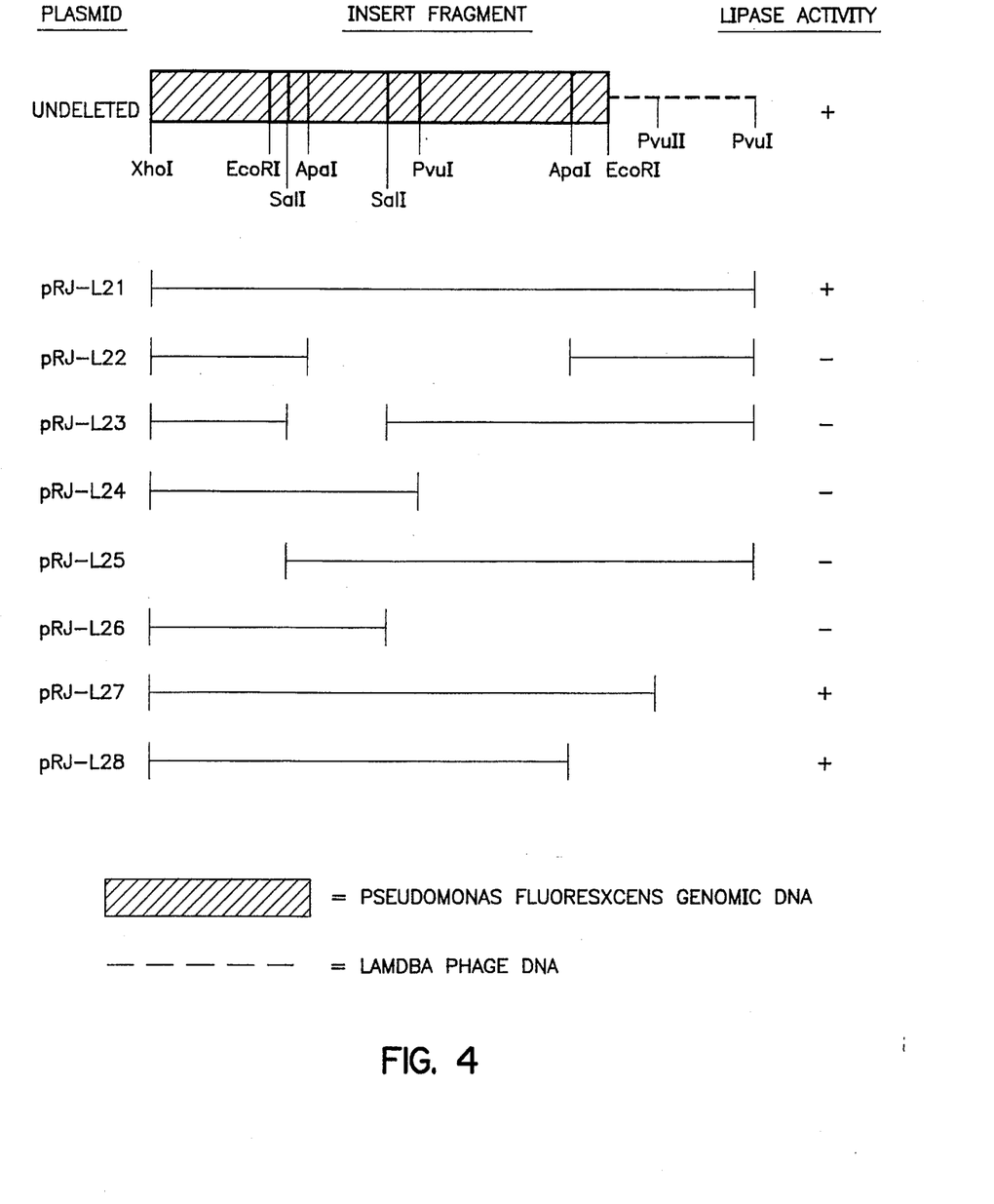
FIG. 4 results from a sublcone analysis of plasmid pRJ-L2 and shows the amount of insert DNA contained within each of the subclones generated from plasmid pRJ-L2. The "undeleted" construct is pRJ-L2. Plasmids pRJ-L21 through pRJ-L28 were derived by removing internal and end terminal sections of the pRJ-L2 insert DNA. The amount of insert DNA remaining in each subclone plasmid is indicated by an unbroken line. Deletions are indicated by open areas within the lines. The ability of each of the subclone plasmids to produce lipolytic activity in transformed *E. coli* is indicated: "+"=capable of producing lipolytic activity, "–"=not capable of producing lipolytic activity.

Subclone plasmids were constructed by removing end terminal and interior regions of the insert DNA and ligating the remaining insert into plasmid pBC-SK+. Insert fragments were detected and verified by agarose gel electrophoresis of restriction endonuclease digested plasmid "miniprep" DNA (as previously described). The ability of each of the subclone transformants to produce a functional Pseudomonas lipase was evaluated by streaking the transformed *E. coli* onto Spirit Blue/chloramphenicol indicator plates and determining if a zone of lipolytic clearing was formed (as described above). The identity of each of the insert fragments as well as the plasmid designation given to the recombinant plasmid containing each individual insert is shown in FIG. 4; also indicated in FIG. 4 is the ability of the insert fragment to produce a functional lipase protein in transformed *E. coli.*

Figure 5:
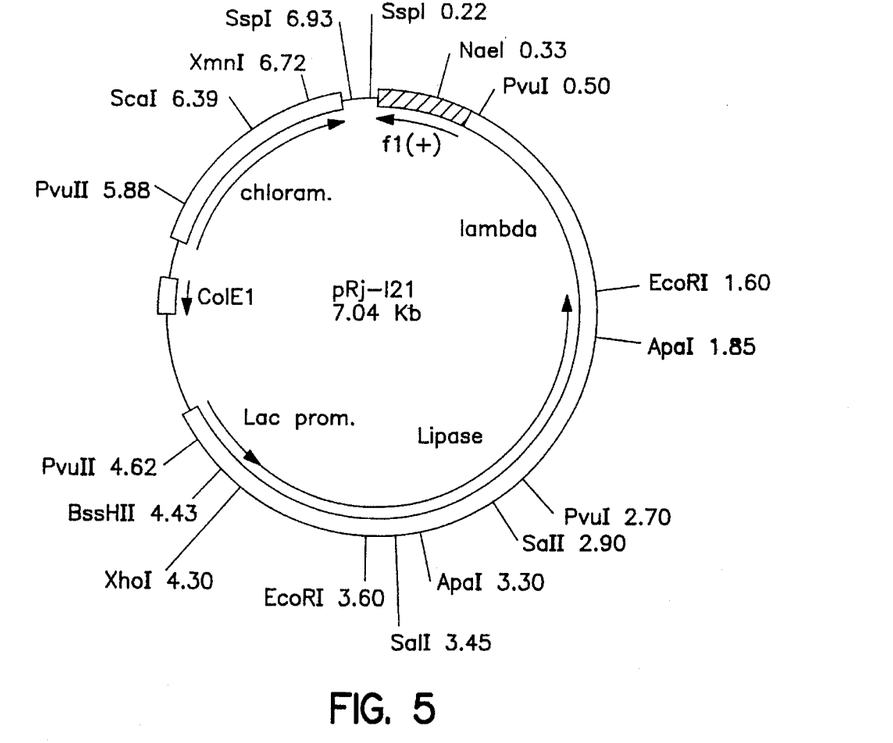
FIG. 5 is a restriction map of lipase expression plasmid pRJ-L21. Plasmid pRJ-L21 was generated during subclone analysis of plasmid pRJ-L2. *E. coli* transformed with plasmid pRJ-L21 produced lipolytic activity. Abbreviations used are as described for FIG. 2.

*E. coli* transformants which contained plasmid pRJ-L21 appeared to form the largest zones of clearing on Spirit Blue indicator plates Plasmid pRJ-L21 was introduced into two additional strains of *E. coli:* XL-1 Blue and BL-21. In each case the transformed cells produced lipolytic activity (as determined by lipolysis on Spirit Blue/chloramphenicol indicator plates). A plasmid map for lipase expression plasmid pRJ-L21 appears in FIG. 5.

H. Characterization of the *P. fluorescens* lipase protein expressed in *E. coli*

Total cellular proteins were isolated from W3110-M25/pRJ-L21 (lipolytic transformant) by the following protocol: a single colony of W3110-M25/pRJ-L21 was inoculated into 2.0 mls of Luria broth plus 30 µg/mL chloramphenicol. This culture was grown overnight on a gyrotory water bath shaker (150 RPM) at 37° C. until late-log phase (OD600 of approximately 3.0). A 1.0 mL sample was removed and transferred to a 1.5-mL microcentrifuge tube. Cells were collected by microcentrifugation at 10,000 RPM, 10 minutes, room temperature. The supernatant was removed by vacuum-aspiration and the cell pellet was resuspended at OD600=60 in TE buffer plus 5 mg/mL lysozyme (Sigma Chemical Company, St. Louis, Mo.). The sample was incubated at room temperature for 10–15 minutes before addition of one volume of 4% sodium dodecyl sulfate (final concentration=2%). The sample was stored at −20° C. overnight prior to analysis. A 10 µL aliquot of this protein preparation was placed into a 2.5 mm well cut into a Spirit Blue agar plate and the plate was placed at 37° C. Within 2 hours, a distinct zone of clearing had surrounded the well, indicating the presence of lipase protein. Parallel protein samples prepared from *E. coli* strains W3110-M25 (no plasmid) or W3110-M25/pBC-SK+ (no insert) displayed no liopolytic activity, indicating that lipolysis was caused by the *P. fluorescens* DNA insert.

The protein samples prepared from W3110-M25, W3110-M25/pBC-SK+, and W3110-M25/pRJ-121 were analyzed by sodium dodecyl sulfate/polyacrylamide gel electrophoresis by the following protocol: a 20 µL sample of protein was transfered to a 1.5-mL microcentrifuge tube and an equal volume of 2× gel loading buffer (125 mM Tris-HCl, pH=6.8; 20% v/v glycerol; 5% v/v β-mercaptoethanol; and 0.025% bromophenol blue) was added. Twenty microliters of each of the protein preparations was electrophoresed on a 10%–20% gradient sodium dodecyl sulfate/polyacrylamide minigel (Integrated Separation Systems, Hyde Park, Mass.) at 50 mA until the tracking dye had reached the bottom of the gel. The gel was then removed from the apparatus and placed in a tray containing 200 mL of a solution of 2.5% (v/v) Triton X-100 (Sigma Chemical Company, St. Louis, Mo.) in dH$_2$O, and incubated at room temperature for 2 hours. The Triton solution was removed and the gel was washed 5 times with sterile dH$_2$O. The gel was then transferred to the bottom of a 150 mm Petri dish and overlayed with 75 mL of molten Spirit Blue/chloramphenicol (cooled to 50° C.). The plate was incubated at 37° C. for 16 hours. A clear band of lipolysis was apparent above the lane in which the proteins derived from W3110-M25/pRJ-L21 were electrophoresed. No lipolytic activity was produced by proteins derived from W3110-M25 (no plasmid control culture) or W3110-M25/pBC-SK+ (no insert transformant control culture).

The molecular weight of the heterologous lipase protein was estimated by sodium dodecyl sulfate/polyacrylamide gel electrophoresis of the three previously described protein samples. Twenty microliters of each of the protein samples was transferred to a 1.5 ml micocentrifuge tube. An equal volume of 2× gel loading buffer was added to each and the samples were incubated at 100° C. for 5 minutes. Twenty-five microliters of each sample was electrophoresed on a 10%–20% gradient sodium dodecyl sulfate/polyacrylamide minigel (Integrated Separation Systems, Hyde Park, Mass.) at 35 mA until the tracking dye had reached the bottom of the gel. The gel was removed from the apparatus and soaked in fixing/staining solution (50% methanol, 40% dH2O, 10% acetic acid, 0.05% Coomassie Briliant Blue) for 4 hours at room temperature. The staining solution was removed and replaced with 200 mls of destaining solution (45% methanol, 45% dH$_2$O, 10% acetic acid). The gel was incubated at room temperature until distinct protein bands were visible against a clear background. Proteins prepared from the lipolytic transformant displayed a band at 50–55,000 Daltons which was not present in the proteins prepared from the control cultures. This band presumably represents the Pseudomonas-derived lipase protein.

A pH optimum for the lipase protein, as expressed in recombinant *E. coli*, has been determined based on the results of the Sigma lipase assay (described below). At an assay temperature of 38° C. the pH optimum is 8.5.

I. Partial DNA Sequence and Deduced Amino Acid Sequence of the Lipase Insert of Plasmid.,pRJ-L21

The DNA sequence of the first 920 bp of the lipase insert of plasmid pRJ-L21 has been determined (starting with the XhoI terminus and working toward the PvuI terminus). This partial DNA sequence data (SEQ. ID. NO. 1) was used to generate a presumed amino acid sequence (SEQ. ID. NO. 2) for the NH2 terminal of the ATCC 13525 lipase protein.

J. Construction of high level lipase expression plasmid pRJ-Ltac1

The XhoI/PvuII fragment of plasmid pRJ-L21 (which encompasses the *P. fluorescens* lipase gene) was removed from the plasmid by digestion with restriction enzymes XhoI and PvuII following the manufacturers suggested reaction conditions. This insert fragment (approximate molecular weight of 2950 bp) was isolated away from the remaining vector sequences by agarose gel electrophoresis as previously described. Insert DNA was purified with Geneclean (Bio 101) as previously described. The end terminus created by digestion with PvuII is blunt-ended, and the XhoI terminal was converted into a blunt end by treatment with mung bean nuclease. The reaction conditions were: 4 mg. XhoI/PvuII insert fragment, 5 mL 10× mung bean nuclease buffer (at 1× concentration=30 mM sodium acetate, pH 5.0; 50 mM sodium chloride; 1 mM zinc acetate; 5% (vol/vol) glycerol; 50 mg/mL bovine serum albumin), 25 units of mung bean nuclease (Stratagene Cloning Systems, La Jolla, Calif.), and sufficient dH$_2$O to bring the total volume to 50 mL. This reaction was incubated at 37° C. for 30 minutes and stopped by the addition of 1 mL 500 mM ethylenediaminetetraacetic acid. The blunt-ended insert DNA fragment was purified with Geneclean (Bio 101) as previously described, and the concentration was estimated by absorbance at 260 nm.

Ptac promoter plasmid pKK223-3 was commercially obtained (Pharmacia LKB Biotechnology, Piscataway, N.J.). Plasmid pKK223-3 was digested with restriction enzyme PstI according to manufacturer's suggested reaction conditions. The cut plasmid was purified with Geneclean (Bio 101) and the PstI termini were converted to blunt ends with mung bean nuclease (as previously described). The blunt-ended linearized vector was purified with Geneclean (Bio 101) and the concentration was estimated by absorbance at 260 nm.

Figure 6:
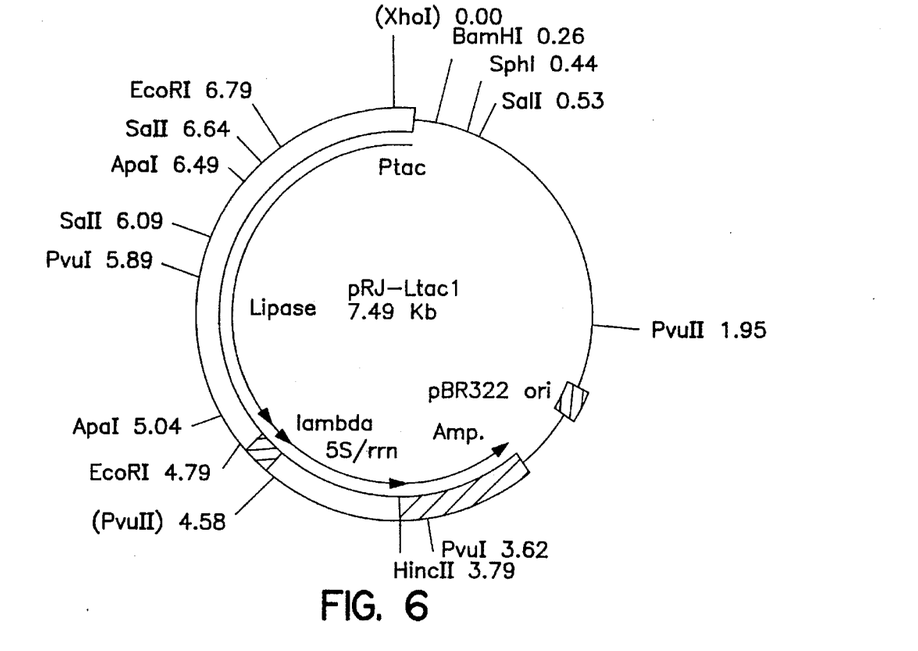

The blunt-ended lipase insert fragment was ligated into the blunt-ended plasmid pKK223-3 by the following reaction: 100 ng vector DNA, a three-fold molar excess of insert DNA, 2 mL of 5× T4 DNA ligase buffer (Bethesda Research Laboratories, as previously described), 1 mL T4 DNA ligase (Bethesda Research Laboratories), and sufficient dH$_2$O to bring the total volume to 10 mL. This reaction was incubated at room temperature for 60 hours. One half of this ligation reaction was used to transform 100 mL. of competent *E. coli* (strain W3310-M25) as previously described. Transformants were selected on Spirit blue agar plates containing 100 mg/mL of ampicillin. Transformants which had taken up a recombinant plasmid (containing the lipase insert fragment) were identified by a clear zone of lipolytic activity surrounding the colony. Lipolytic transformants were used to prepare plasmid "minipreps" as previously described. In every case the XhoI terminal of the insert fragment was situated adjacent to the Ptac promoter, suggesting that expression of the lipase protein was directed by transcription from the tac promoter. A diagram of lipase expression plasmid pRJ-Ltac1 appears as FIG. 6. Miniprep DNA of this recombinant plasmid was used to transform *E. coli* strain BL21 (as previously described). This transformant (BL21/pRJ-Ltac1) produced an extremely large zone of lipolytic activity on Spirit Blue agar plates.

K. Functional activity of the *P. fluorescens* ATCC 13525 lipase protein expressed in recombinant *E. coli*

*E. coli* strain BL21 transformed with plasmids pRJ-L21 or pRJ-Ltac1 was analyzed for lipase activity by the following protocol. Transformants were grown in 250-mL shake flasks in Luria broth or Lennox broth [1% Bacto tryptone (Difco Laboratories, Detroit, Mich.); 0.5% yeast extract (Difco Laboratories, Detroit, Mich.); 0.2% glucose; 0.05% NaCl; pH=7.5] supplemented with 30 µg/mL chloramphenicol (pRJ-L21 transformant) or 100 mg/mL ampicillin (pRJ-Ltac1 transformant) at 30° C. on a gyrotory water bath shaker (150 RPM) until late-log phase (OD600 of 4.0–4.5). A 1.0 mL aliquot was removed and transferred to a 1.5 mL microcentrifuge tube. Cells were pelleted by microcentrifugation at 13,000×g for 5 minutes at room temperature. The supernate was removed by vacuum-aspiration and the cell pellet was resuspended in 980 gL of TE buffer. This cell suspension was incubated at room temperature for 15 minutes. Twenty microliters of a 10% solution of sodium dodecyl sulfate in dH$_2$O was added and the cells were vortex-mixed (Vortex Genie; Fisher Scientific, Pittsburgh, Pa.; speed setting "9") for 20 seconds at 15-minute intervals for a total of 60 minutes. This cell "lysate" was stored a 4° C. for 16 hours before being assayed for lipase activity using the Sigma lipase reaction. The Sigma lipase assay utilizes a pH stat to measure the amount of free fatty acid liberated from a solution of triglyceride by lipase-catalyzed lipolysis. A 10 µL aliquot of cell lysate was added to 20 mL of lipase substrate solution [300 mL of Sigma lipase substrate (Sigma Chemical Company, St. Louis, Mo.); 120 ml of 3.0M NaCl; 120 mL of 1.5% (w/v) sodium taurocholate (Sigma); and 60 mL of 0.075% CaCl$_2$], and liberated fatty acids were titrated with controlled additions of 0.01N NaOH. One unit of enzyme activity was defined as the amount of enzyme which liberates 1 µmol of titratable triglyceride per minute at 37° C., pH 8.5.

| Results: | | |
|---|---|---|
| Strain | Growth Media | Lipase Titer |
| BL21 | Luria | <2 |
| BL21/pBC-SK+ | Luria/chloramphenicol | <2 |
| BL21/pRJ-L21 | Luria/chloramphenicol | 69 |
| BL21 | Lennox | <2 |
| BL21/pBC-SK+ | Lennox/chloramphenicol | <2 |
| BL21/pRJ-L21 | Lennox/chloramphenicol | 363 |

Transformants BL21/pRJ-L21 and BL21/pRJ-Ltac1 were also tested for lipase expression in large scale cultures. Medium A=defined minimal *E. coli* medium/0.5% glucose; medium B=Lennox broth/glycerol, medium C=defined *E. coli* minimal medium/glycerol.

| Strain | Culture Size | Medium | Lipase Titer |
|---|---|---|---|
| BL21/pRJ-L21 | 15 liters | A | 1,371 |
| BL21/pRJ-L21 | 500 liters | B | 956 |
| BL21/pRJ-Ltac1 | 15 liters | A | 19,310 |
| BL21/pRJ-Ltac1 | 250 liters | C | 14,062 |

L. Applications of the recombinant *P. fluorescens* ATCC 13525 lipase in recent drug development projects 1) Thromboxane Antagonist: The recombinant lipase enzyme was used to catalyze the stereoselective hydrolysis of (exo, exo)-7-oxabicyclo[2.2.1]heptane-2,3-dimethanol diacetate ester 1 to the corresponding monoacetate ester 2, as shown in Reaction Scheme 1. The chiral monoacetate ester 2 was oxidized to its corresponding aldehyde and subsequently hydrolyzed to give lactol 3. Chiral lactol 3 is the key intermediate required for the synthesis of the new thromboxane antagonist 4.

Reaction Scheme 1

-continued
Reaction Scheme 1

4

The enzymatic reaction mixture for the hydrolysis contained 36 mL of 50 mM potassium phosphate buffer (pH 7.0), 4 mL of toluene, 200 mg of diacetate ester (1) and 1 gram of recombinant lipase powder. The reaction was carried out at 5° C. in a pH stat with continuous mixing for 48 hours. The pH was maintained at 7.0 with 1.0N NaOH.

The hydrolysis of 1 to the corresponding monoacetate ester 2 was monitored by gas chromatography using a Hewlett-Packard HP-5 capillary column (5% diphenyl, 95% dimethylpolysiloxane, 25 m×0.2 mm, 0.11 μm film thickness) at 150° C. (oven), 250° C. (injection), 250° C. (detector). The carrier gas was helium flowing at the rate of 50 mL/min. Samples (2 mL) were extracted with 4 mL of ethyl acetate. Ethyl acetate was centrifuged to separate and filtered through a LID/X filter (0.2 μm) and used for GC analysis. The retention time of 1 and 2 were 6 and 4.13 minutes, respectively.

The optical purity of 2 was determined by chiral HPLC. The separation of the two enantiomers was acheived using a Bakerbond Chiralcel OB column at ambient temperature. The mobile phase was 70% hexane and 30% isopropanol, the flow rate was 0.5 mL/min. The detection wavelength was 220 nm. The retention time of the (−)-enantiomer is 8.5 minutes, the retention time of the (+)-enantiomer is 11.45 minutes.

| Results: | | | |
|---|---|---|---|
| Diacetate 1 (mg/mL) | (−)-monoacetate (mg/mL) | Yield (%) | Optical Purity (%) |
| 0.45 | 3.5 | 85 | 97 |

2) Captopril: The recombinant lipase enzyme was used for the stereoselective hydrolysis of 3-acetyl/thio-2-methyl propanoic acid (racemic 2) to yield S-(−)-2, R(+)-3-mercapto-2-methyl propanoic acid 5 and acetic acid 4, as shown in Reaction Scheme 2. S-(−)-2 is a key chiral intermediate for the synthesis of captopril, an antihypertension drug. In this reaction the recombinant lipase enzyme is used to catalyze the hydrolysis of the thioester bond of the undesired R(+) enantiomer of racemic 2.

Reaction Scheme 2

-continued
Reaction Scheme 2 captopril

The reaction mixture for the hydrolysis of 3-acetylthio-2-methylpropanoic acid contained 0.1M substrate, 25 mL of 1,1,2-trichloro-1,2,2-trifluorethane (CFC-113), 250 mg of recombinant lipase powder, and 0.1% (v/v) water. The reaction was conducted at 30° C., 280 RPM on a rotary shaker in a closed flask. As the hydrolysis of 3-acetylthio-2-methylpropanoic acid proceeds, the remaining non-hydrolyzed substrate becomes increasingly enriched in the desired S-enantiomer.

The hydrolysis of 3-acetylthio-2-methylpropanoic acid was monitored by HPLC analysis of reaction mixture samples following filtration (0.2 μm filter) to remove the insoluble enzyme. A Whatman partisil 5 ODS-3 column (25 cm, C18 reverse phase) was used with a mobile phase consisting of 70% (v/v) 0.05M $KH_2PO_4$, pH=3.0, and 30% (v/v) methanol. Column temperature was 40° C., flow rate was 1 ml/min, and the detection wavelength was 230 nm. Under these conditions, the retention times for 2 and 5 were 11.8 and 5.91 minutes, respectively. The determination of optical purity of S(−)-2 was carried out by treating the samples with thionyl chloride to form the corresponding acid chloride which was subsequently reacted with d-2-octanol to yield the diastereomers. Gas chromatography was used to separate the diastereomers. In a vial, 1 mL of reaction mixture filtrate (3 mg) was evaporated to remove solvent. One mL of 10% thionylchloride solution (10% thionyl chloride in hexane containing 2.5 μL of dimethylformamide) was added to the vial, which was vortex mixed and incubated at room temperature for 30 minutes. Following incubation, the reagent was removed by nitrogen evaporation at 50° C. To the dried residue, 0.3 mL of the d-2-octanol solution (8% d-2-octanol in toluene) was added and the sample was incubated at 60° C. for 30 minutes. Solvent was then nitrogen-evaporated at 50° C. The dried residue was dissolved in 0.5 mL of methylene chloride and assayed by gas chromatography. A Hewlett-Packard fused silica capilary column (cross linked methyl silicone, 15 meters, 1.0 mm film thickness, 0.31 mm I.D.) was used at an injection temperature of 250° C., column temperature of 160° C., and detector temperature of 250° C. The retention times for the R(+)-2 methylpropanoic acid and the S(−)-2 were 13.2 and 13.9 minutes, respectively.

| Results | | |
|---|---|---|
| Reaction Time (hours) | Reaction Yield S(−)-2 (%) | Optical Purity S(−)-2 (%) |
| 22 | 25 | 97 |

3) Zofenopril As shown in Reaction Scheme 3, the recombinant *P. fluorescens* lipase was used to catalyze the esterification of undesired enantiomer of racemic 1 to yield the R(+)methyl ester of 2 and unreacted acid enriched in the desired S(−)-1, a key intermediate for the synthesis of zofenopril (3). The key intermediate, S-(−)-3-benzoylthio- 2-methyl propanoic acid (S-(–)-1), was made in high optical purity by the stereoselective esterification of racemic 1 with methanol in an organic solvent system.

Reaction Scheme 3

The enzymatic reaction mixture for the esterification contained 0.1M of 1, 0.4M methanol, 0.1% water, and 1 g of recombinant lipase powder in 10 mL of toluene. The reaction was conducted at 40° C. and 280 RPM. Periodically, samples were taken and analyzed by GC to determine the yield and optical purity of the product.

The esterification of 1 was monitored by gas chromatography of reaction mixture samples using a Hewlett-Packard fused silica capillary column (cross-linked methyl silicone, 15 meters, 1.0 μm film thickness, 0.31 mm I.D.) at 215° C. oven temperature, 250° C. injection temperature, and 250° C. detection temperature. The retention time for 1 was 3.8 minutes; for the corresponding methyl ester, 3.1 minutes. The optical purity of 1 was determined by treating samples with thionyl chloride and reacting the acid chloride formed with D-2-octanol to yield the diastereomers. In the procedure used, 1 mL of reaction mixture filtrate (3 m of 1) was evaporated to remove the solvent. One mL of 10% thionyl chloride solution in n-hexane containing 2.5 μg dimethylformamide was added to the vial, mixed thoroughly on a vortex mixer and incubated at room temperature for 30 minutes. The reagent was subsequently evaporated under a gentle stream of nitrogen at 50° C. To the dried residue, 0.3 mL of D-2-octanol was added, mixed thoroughly, and incubated at 60° for 30 minutes. Octanol was evaporated under a stream of nitrogen at 50° C. and the residue was dissolved in 0.5 mL methylene chloride. Diastereomers were analyzed by GC using a Hewlett-Packard fused silica capillary column at 215° C. oven temperature, 250° C. injection temperature, and 250° C. detector temperature. The retention times for the esters of the L- and D-enantiomers were 14.8 and 16.0 minutes, respectively.

| | Results | |
|---|---|---|
| Reaction Time (hours) | Reaction Yield S(–)-2 (%) | Optical Purity S(–)-2 (%) |
| 27 | 35 | 96 |

---

What is claimed is:

1. An isolated nucleic acid molecule comprising a sequence encoding a lipase, wherein the lipase has the amino acid sequence of SEQ. ID. NO.: 2.

2. The nucleic acid molecule according to claim 1 having the nucleotide sequence of SEQ. ID. NO.: 1.

3. A DNA molecule having a DNA sequence which is complementary to the DNA sequence according to claim 2.

4. An expression vector encoding a polypeptide which comprises a lipase having the amino acid sequence of SEQ. ID. NO.: 2.

5. A prokaryotic or eukaryotic host cell containing the expression vector according to claim 4.

6. A method for producing a polypeptide molecule which comprises a lipase having the amino acid sequence of SEQ. ID. NO.: 2, comprising culturing a host cell according to claim 5 under conditions permitting expression of the polypeptide.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 926 base pairs
        ( B ) TYPE: nucleic acid
        ( C ) STRANDEDNESS: double
        ( D ) TOPOLOGY: linear     ( i i ) MOLECULE TYPE: DNA (genomic)

( i x ) FEATURE:
        ( A ) NAME/KEY: CDS
        ( B ) LOCATION: 525..926

( x i ) SEQUENCE DESCRIPTION: SEQ ID NO:1:

```
CTCGAGGTGT  CCGGCACGCT  GGGCTGGCAG  CACAACCTGA  GCAGCACCGA  TTCCGAACAG      60

CACCTGGCGT  TTGCTTCGGG  CGGTCCGGCG  TTTGCGGTGG  AAAGTGCACC  GATGGTCGGT     120

GATGCGGCAT  TGGTGGGCGC  GCGGGTCAGC  CTGGCGTTGA  GCAAGGACGC  GCGGGTGAAC     180

TTTGATTACA  ACGGCCTGCT  GGCCAGCAAG  GAAAAAGTCC  ACGGGGTGGG  GTTGAGCCTC     240

GACTGGGCGT  TCTAAACAAG  CACGACCTGC  TTAATGTGGA  ACCGGACTTT  ATGTGGGAGC     300

GGGCTTGCTC  GCGAAAGCGG  TGTGTCAGTT  AACGGCCTCA  TTGGCTGGTA  CAGCGTATTC     360

GCGAGCAAGC  CCGCTCCCAC  ATTTGGATCA  CCGGGAATCA  GGTAGATTTG  CGTCAGTCTG     420

GAGGCCATCA  TCGCAGGCAA  GCCAGTTCCC  ACATAAAGCC  TGTCCCTCAG  GGGCAACGGG     480
```

```
TGTTTTCGCT  TTCTCTACAA  ATCCAACAAC  AGAGAGGCAC  TACC ATG GGT ATC TTT            536
                                                     Met Gly Ile Phe
                                                      1

GAC TAT AAA AAC CTC GGC ACC GAG GGT TCC AAA GCG CTG TTT GCC GAC                 584
Asp Tyr Lys Asn Leu Gly Thr Glu Gly Ser Lys Ala Leu Phe Ala Asp
 5               10              15                          20

GCC ATG GCG ATC ACG TTG TAC TCC TAC CAC AAC CTG GAT AAC GGC TTT                 632
Ala Met Ala Ile Thr Leu Tyr Ser Tyr His Asn Leu Asp Asn Gly Phe
                 25              30                      35

GCC GTG GGT TAC CAG CAC AAT GGC TTG GGG CTT GGT TTG CCG GCC ACG                 680
Ala Val Gly Tyr Gln His Asn Gly Leu Gly Leu Gly Leu Pro Ala Thr
             40              45                      50

CTG GTG GGT GCA CTG CTC GGC AGC ACG AAT TCA CAG GGT GTC ATT CCG                 728
Leu Val Gly Ala Leu Leu Gly Ser Thr Asn Ser Gln Gly Val Ile Pro
         55              60                  65

GGC ATT CCC TGG AAC CCG GAT TCG GAA AAA GCC GCG CTG GAG GCG GTG                 776
Gly Ile Pro Trp Asn Pro Asp Ser Glu Lys Ala Ala Leu Glu Ala Val
         70              75              80

CAA AAC GCC GTT GGA CGC CCA TCA GTG CAA GCA CCC TCG GCT ACG GCG                 824
Gln Asn Ala Val Gly Arg Pro Ser Val Gln Ala Pro Ser Ala Thr Ala
 85              90              95                         100

GCA AAG TCG ACG CGC GCG GCA CGT ACT TTG GCG AAA AAG CCG GTT ACA                 872
Ala Lys Ser Thr Arg Ala Ala Arg Thr Leu Ala Lys Lys Pro Val Thr
                 105             110                     115

CCA CCG CTC AGG TCG AGG TGC TGG GCA AGT ACG ATG ACG CCG GCA AAT                 920
Pro Pro Leu Arg Ser Arg Cys Trp Ala Ser Thr Met Thr Pro Ala Asn
             120             125                     130

TGC TGG                                                                         926
Cys Trp
```

( 2 ) INFORMATION FOR SEQ ID NO:2:

( i ) SEQUENCE CHARACTERISTICS:
        ( A ) LENGTH: 134 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met Gly Ile Phe Asp Tyr Lys Asn Leu Gly Thr Glu Gly Ser Lys Ala
 1               5              10                      15

Leu Phe Ala Asp Ala Met Ala Ile Thr Leu Tyr Ser Tyr His Asn Leu
                 20              25              30

Asp Asn Gly Phe Ala Val Gly Tyr Gln His Asn Gly Leu Gly Leu Gly
             35              40              45

Leu Pro Ala Thr Leu Val Gly Ala Leu Leu Gly Ser Thr Asn Ser Gln
         50              55              60

Gly Val Ile Pro Gly Ile Pro Trp Asn Pro Asp Ser Glu Lys Ala Ala
 65              70              75                      80

Leu Glu Ala Val Gln Asn Ala Val Gly Arg Pro Ser Val Gln Ala Pro
                 85              90              95

Ser Ala Thr Ala Ala Lys Ser Thr Arg Ala Ala Arg Thr Leu Ala Lys
             100             105             110

Lys Pro Val Thr Pro Pro Leu Arg Ser Arg Cys Trp Ala Ser Thr Met
             115             120             125

Thr Pro Ala Asn Cys Trp
             130
```